US00PP28124P3

(12) United States Plant Patent
Papalini

(10) Patent No.: US PP28,124 P3
(45) Date of Patent: Jun. 20, 2017

(54) ARTICHOKE PLANT NAMED 'PIETRO #3'

(50) Latin Name: *Cynara scolymus*
Varietal Denomination: PIETRO #3

(71) Applicant: Pietro Papalini, Barletta (IT)

(72) Inventor: Pietro Papalini, Barletta (IT)

( * ) Notice: Subject to any disclaimer, the term of this patent is extended or adjusted under 35 U.S.C. 154(b) by 0 days.

(21) Appl. No.: 13/998,849

(22) Filed: Dec. 13, 2013

(65) Prior Publication Data

US 2014/0317802 P1 Oct. 23, 2014

Related U.S. Application Data

(63) Continuation of application No. 13/854,894, filed on Apr. 1, 2013, now abandoned.

(60) Provisional application No. 61/686,292, filed on Apr. 2, 2012.

(51) Int. Cl.
*A01H 5/02* (2006.01)

(52) U.S. Cl.
USPC ..... Plt./258
CPC ..... *A01H 5/025* (2013.01)

(58) Field of Classification Search
USPC ..... Plt./258
See application file for complete search history.

*Primary Examiner* — Susan McCormick Ewoldt
(74) *Attorney, Agent, or Firm* — Ballew Law

(57) ABSTRACT

A new cultivar of *Cynara* named 'PIETRO #3' that is distinguishable by high yield of immature edible flower buds that are tight, globe-shaped, and dark red in color. In combination these traits set 'PIETRO #3' apart from all other existing varieties of *Cynara* known to the inventor.

2 Drawing Sheets

Genus and species: *CYNARA scolymus.*
Variety denomination: 'PIETRO #3'.

STATEMENT REGARDING FEDERALLY SPONSORED RESEARCH OR DEVELOPMENT

None

CROSS-REFERENCE TO RELATED APPLICATIONS

This is a Non-Provisional Plant Patent Application based Continuation of currently pending Non-Provisional application Ser. No. 13/854,894 filed Apr. 1, 2013, which claimed priority to upon Provisional patent application Ser. No. 61/686,292 as filed on Apr. 2, 2012, and claims priority under 35 U.S. C. 199(e). Each patent application identified above is incorporated here by reference in its entirety to provide continuity of disclosure.

BACKGROUND OF THE INVENTION

The present invention relates to a new and distinct cultivar of *CYNARA* known commonly as Italian purple artichoke a perennial herb that is grown as a food crop for the production of edible vegetable delicacies. The new invention is known botanically as *CYNARA scolymus* and will be referred to hereinafter by the cultivar name 'PIETRO #3'. *Cynara* is in the family Asteraceae, formerly known as Compositae.

An individual plant of *Cynara scolymus* 'PIETRO #3' is comprised of main stem, lateral stems, leaves, and immature flower buds known as involucra. Each involucrum is made up of imbricate phyllaries also known as involucral bracts. Freshly harvested immature flower buds can be baked, grilled, boiled, or steamed, making the smooth part of the bracts, the setaceous receptacle, and the uppermost part of the peduncle, edible. If not harvested, but permitted to mature, flower buds will develop into flower heads known as capitula.

The new *Cynara* variety named 'PIETRO #3' was derived from a formal plant-breeding program that originated in Tarquinia, Italy and was in effect for more than twenty years. The program began with the goal of producing new hybrid plants that yield homogenous red and green edible artichokes. The inventor in Lompoc, Calif. has received and developed 42 lines of artichoke plants, from this specific breeding program in Italy. Bi-color Italian artichokes are popular in Italy and referred to as Romanesco artichokes, however, the solid red color is less desirable in Italy.

As part of the breeding program in Tarquinia, Italy, deliberate controlled cross-pollination took place in 2007 that resulted in whole plants, one of which yielded immature flower buds that were predominantly solid red in color as opposed to the desired bi-color. Vegetative propagules called ovoli were removed from said plant and transported to Lompoc, Calif. in 2008 where they were given to the inventor in Lompoc for further consideration and evaluation of potential commercial value in the United States. The inventor subsequently learned of the death of the individual who had supervised the breeding program in Italy. The actual parents of the 2007 cross are unknown, as they were unnamed, and identified only as proprietary plant material used in the Tarquinia breeding program for the purposes of cross-pollination.

In Lompoc, Calif., under the direct supervision of the inventor the vegetative propagules were field grown to maturity, after which 'PIETRO #3' was selected by the inventor in early 2010 based on the criteria of artichoke color, shape, size, and yield. The new *Cynara* plant variety named 'PIETRO #3' is a hybrid selection made by the inventor in Lompoc, Calif. and derived from the original propagule collection sent from Tarquinia, Italy. The original propagule collection was derived from the deliberate controlled cross-pollination of an individual unnamed *Cynara scolymus* (unpatented) as the seed parent and an individual unnamed *Cynara scolymus* (unpatented) as the pollen parent. Other than genus and species, the identification of the parentage is limited to—proprietary plant material from the original breeding program in Tarquinian. Italy.

The closest comparison plant is *Cynara scolymus* 'BCV 8-11' (U.S. Plant Pat. No. 16,429). The comparison plant yields immature artichoke flower buds used as miniature gourmet delicacies, whereas immature artichoke flower buds from 'PIETRO #3' range in size from small to medium. The new cultivar 'PIETRO #3' is distinguishable from the comparison plant by immature artichoke bud size, shape, color, and yield.

The new *Cynara* variety named 'PIETRO #3' is characterized by upright habit, and tight, globe-shaped, dark red immature flower buds. 'PIETRO #3' exhibits high yield, producing 1 central and up to 34 lateral immature flower buds the first year. Asexual propagation is accomplished by the methods of division and tissue culture. Cultural requirements include full sun, well-draining soil, and moderate water. Hardiness is classified as USDA Zone 6.

The first asexual propagation of the new variety named 'PIETRO #3' was conducted in the inventor's laboratory in Lompoc, Calif. under the direct supervision of the inventor in 2010. The method used was tissue culture. Since that time field propagation has been carried out using the method of division. Under careful observation, 'PIETRO #3' has been determined uniform, stable and true to type in subsequent generations of asexual propagation.

SUMMARY OF THE INVENTION

The following traits have been repeatedly observed and represent the distinguishing characteristics of the new *Cynara* cultivar named 'PIETRO #3'. These traits in combination distinguish 'PIETRO #3' from all other existing varieties of *Cynara* known to the inventor. 'PIETRO #3' has not been tested under all possible conditions and phenotypic differences may be observed with variations in environmental, climatic, and cultural conditions, however, without any variance in genotype.

1. 'PIETRO #3' yields 1 central and up to 34 lateral immature flower buds the first year.
2. The immature flower buds of 'PIETRO #3' are tight and globe-shaped.
3. The immature flower buds of 'PIETRO #3' are dark red in color.
4. The immature flower buds from 'PIETRO #3' are harvested in range of sizes.
5. 'PIETRO #3' is asexually propagated using the methods of tissue culture and division.
6. 'PIETRO #3' grows in full sun and well-draining soil, with moderate water.
7. 'PIETRO #3' is hardy to USDA Zone 6.

BRIEF DESCRIPTION OF THE DRAWINGS

The accompanying color drawings illustrate the overall appearance of the new *Cynara* cultivar named 'PIETRO #3' showing color as true as is reasonably possible to obtain in color reproductions of this type. Color in the drawings may differ from color values cited in the detailed botanical description, which accurately describe the actual color of the new variety 'PIETRO #3'. Drawing labeled FIG. 1 was made in March 2009 of a field grown plant in Lompoc, Calif. Drawing labeled FIG. 2 was made in November 2010 in Arroyo, Grande Calif. of a plant field grown in Lompoc.

Drawing labeled

Drawing labeled

Figure 1:
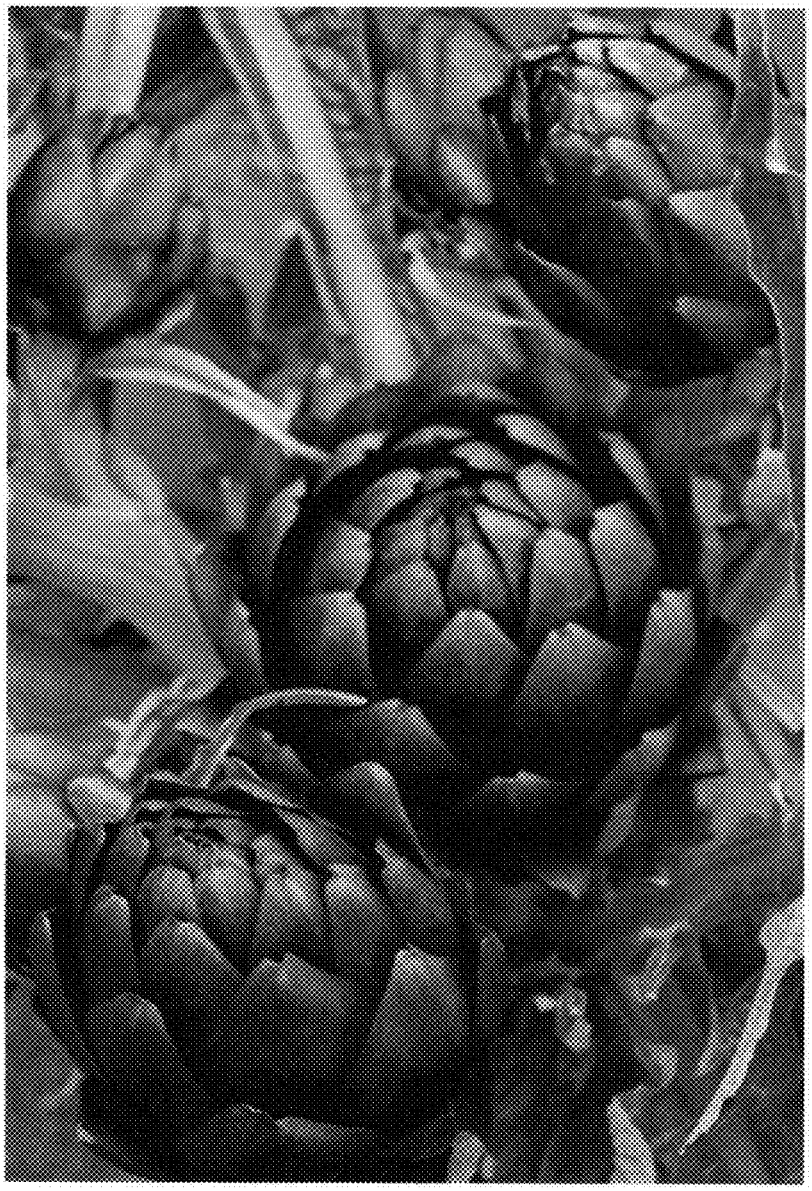
FIG. 1 depicts central and lateral immature flower buds of 'PIETRO #3'.
Figure 2:
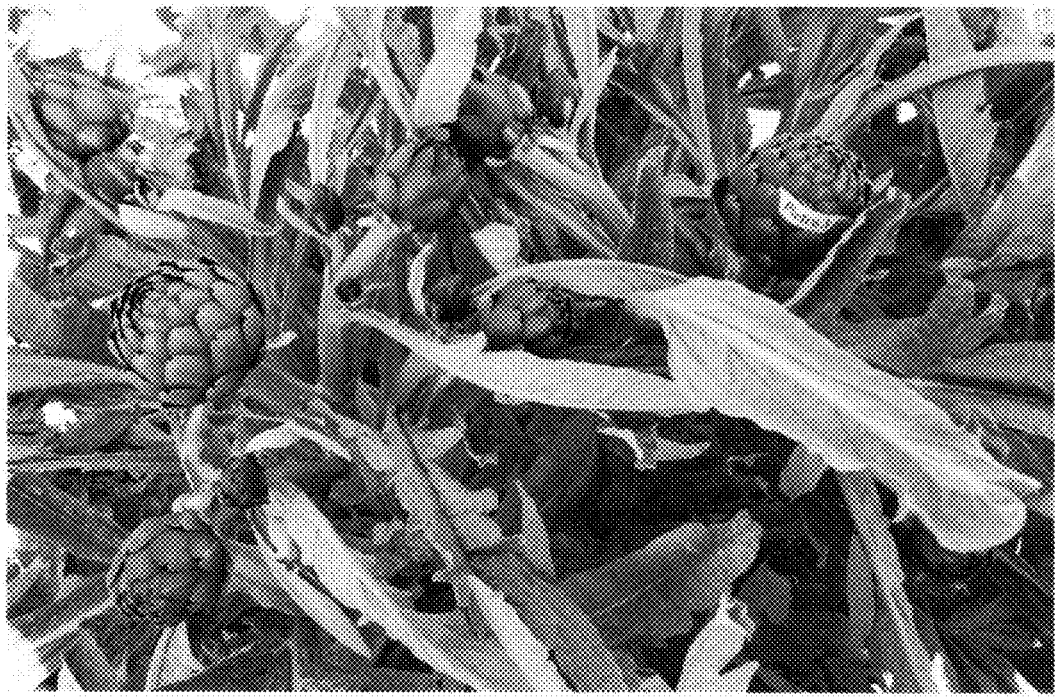
FIG. 2 depicts the range in size of dark red artichokes for harvest.

The drawings were made using conventional techniques and although immature flower bud and foliage color may appear different from actual color due to light reflectance, it is as accurate as possible by conventional photography.

BOTANICAL DESCRIPTION OF THE PLANT

The following is a detailed botanical description of the new *Cynara* cultivar named 'PIETRO #3'. Color determinations are in accordance with The 2001 Royal Horticultural Society Colour Chart of London, England, except where general color terms of ordinary dictionary significance are used. The following observations, measurements and values describe the new cultivar named 'PIETRO #3' as grown in Lompoc, Calif. under conditions used in horticultural practice.

TABLE 1 sets forth some of the distinguishing characteristics of 'Pietro #3' as compared to 'BCV 8-11' (U.S. Plant Pat. No. 16,429) and to 'Z530' (U.S. Plant Pat. No. (21,688):

| Characteristic | 'Pietro #3' | 'BCV 8-11' | 'Z530' |
|---|---|---|---|
| Immature bud size at harvest | 6-18 cm (height) × 4.5-20 cm (diameter) | 9 cm (height) × 9 cm (diameter) | 13.5 cm (height) × 20 cm (diameter) |
| Immature bud shape | Globe | Oval with reflexive bracts | Oblate |
| Immature bud weight at harvest | Avg. 300-450 grams | Avg. 150-200 grams | Avg. 561.90 |
| Immature bud - Outer bract color | Dorsal - N186C, tints of N79A Ventral - 147C, tints of N79A | Greyed purple group between 187A and 187B | Dorsal - 147C (147D-148C) Ventral - 147C (147D-148C) |
| Immature bud - Inner bract color | Dorsal - N186C, tints of N79A Ventral - 147C, tints of N79A | Greyed purple group between 187B and 187C | Dorsal - 155D (155D-155A) Dorsal - 155D (155D-155A) |

Lompoc, Calif. is located on the central coast in Santa Barbara County. Conditions in Lompoc vary with air temperatures ranging from 15.5° Centigrade to 26.6° Centigrade. The relative humidity is generally high. Prevailing winds are northwesterly and rainfall averages twelve inches per year. The plants were grown in rows where row spacing (bed centers) was at 3 meters and individual plant spacing at 120 cm. Data was collected in March 2009 from field grown plants. Growing requirements are similar to the species.

Botanical classification: *CYNARA scolymus* 'PIETRO #3'.

Family: Asteraceae (formerly Compositae).

Genus: *CYNARA*.

Species: *scolymus*.

Denomination: 'PIETRO #3'.

Common name: Italian purple artichoke.

Commercial classification: Food crop.

Use: Production of edible vegetable delicacies.

Parentage: *Cynara scolymus* 'PIETRO #3' is a hybrid plant selection derived from vegetative propagules grown to maturity in Lompoc, Calif., that resulted from deliberate controlled cross-pollination of unknown parents from the breeding program in Tarquinia, Italy.

Plant description:

*Habit*.—Upright.

*Vigor*.—Vigorous.

*Type*.—Perennial herb.

*Height*.—140 cm.

*Width*.—198 cm.

*Root system*.—Thick and fibrous.

*Hardiness*.—USDA Zone 6.

*Propagation method*.—Division and tissue culture.

*Crop time* (*average*).—6-12 months to produce a harvestable crop of edible immature flower buds from tissue culture.

*Disease resistance*.—None known to the inventor.

*Pest and disease susceptibility*.—None known to the inventor.

*Cultural requirements*.—Grow in full sun and well-draining soil, with moderate water.

*Stem*.—Branching habit (range): Basal to caulescent. Stem quantity (range): 10-12 per individual plant. Length (range): 31 cm. to 50 cm. Diameter (range): 2.50-3.50 cm. Surface: Furrowed and tomentose. Shape: Columnar. Strength: Rigid. Color: 138B. Internode (range): 7 cm. to 20 cm.

*Foliage*.—Type: Evergreen. Arrangement: Alternate. Division: Simple. Margin (range): Entire to lobed. Quantity (range): 50-88 leaves per individual 12-month old plant. Shape: Lacerate. Attachment: Sessile Leaf color (abaxial surface): 189D. Leaf color (adaxial surface): 148A. Length (range): 21 cm. to 100 cm. Width (range): 11 cm. to 40 cm. Apex: Acute. Base: Truncate. Lobe quantity (range): 7-14 lobes per leaf. Lobe apex (range): Acute. Lobe length (range): 3 cm. to 20 cm. Lobe width (range): 2 cm. to 6 cm. Venation pattern (range): Pinnate to reticulate. Vein color (abaxial surface): 189A. Vein color (adaxial surface): 148D. Abaxial surface: Tomentulose. Adaxial surface (range): Glabrous to pubescent. Appearance (abaxial surface): Dull. Appearance (adaxial surface): Semi-glossy. Stipules: None observed. Fragrance: None observed. Angle of leaf to stem (average): 45°.

Involucrum (immature flower bud):

*Shape*.—Globe.

*Apex* (*range*).—Rounded to Obtuse.

*Base*.—Truncate.

*Central bud height* (*average*).—18 cm.

*Central bud diameter* (*average*).—20 cm.

*Lateral bud height* (*range*).—6 cm. to 17 cm.

*Lateral bud diameter* (*range*).—4.50 cm. to 16 cm.

*Phyllary* (*involucral bract*).—Arrangement: Imbricate. Outer bract quantity (range): 20 to 40 per involucrum. Inner bract quantity (average): 20 to 30 per involucrum. Outer bract shape: Ovate. Inner bract shape: Oblong. Outer bract margin: Entire. Inner bract margin: Entire. Outer bract apex: Retuse. Outer bract base: Truncate. Inner bract apex: Retuse. Inner bract base: Truncate. Bract base width (range): 2.5 cm. to 4 cm. Spine: Present. Spine shape: Triangular. Spine color: N79A. Spine dimensions (average): <2 mm. in height and width. Outer bract texture (after cooking): Smooth. Inner bract texture (after cooking): Smooth. Outer bract height (range): 7 cm. to 8.50 cm. Outer bract width (range): 3 cm. to 5.25 cm. Inner bract height (range): 3.25 cm. to 7.25 cm. Inner bract width (range): 0.75 cm. to 5 cm. Outer bract surface (ventral and dorsal): Glabrous. Inner bract surface (ventral and dorsal): Glabrous. Outer bract color (dorsal surface): N186C with tints of N79A. Outer bract color (ventral surface): 147C with tints of N79A. Inner bract color (dorsal surface): N186C with tints of N79A Inner bract color (ventral surface): 147C with tints of N79A. Outer bract appearance: Matte. Inner bract appearance: Glossy. Receptacle shape: Concavo-convex. Receptacle diameter (range): 3.50 cm. to 7.50 cm. Receptacle depth (range): 0.5 cm. to 1 cm. Receptacle color: 161D (161D-161B). Receptacle texture (after cooking): Setaceous. Pappus height (range): 0.70 cm. to 2.75 cm. Pappus diameter (range): 3.10 cm. to 7.50 cm. Pappus color: 158D (158D-158B). Bristle quantity: >150. Bristle shape: Filament. Bristle color: 158D (158D-158B). Bristle length (range): 0.70 cm. to 2.75 cm. Bristle width (average): <1 mm. Bristle texture: Sericeous.

*Peduncle shape*.—Columnar.

*Peduncle length* (*range*).—28 cm. to 31 cm.

*Peduncle diameter* (*range*).—2 cm. to 3 cm.

*Peduncle color*.—147C.

*Peduncle strength*.—Rigid.

*Peduncle surface*.—Fluted and tomentose.

*Duration of cold storage* (*range*).—22-24 days.

*Cold storage temperature* (*range*).—1° to 2° Centigrade.

*Cold storage response*.—Negligible softening at stem cut.

*Shelf life* (*range*).—22-28 days under mist.

*Weight* (*range*).—300-450 grams.

Mature inflorescence:

*Type*.—Capitula.

*Persistent or self-cleaning*.—Persistent.

*Shape*.—Globe.

*Appearance*.—Thistle-like.

*Depth* (*average*).—18 cm.

*Diameter* (*average*).—20 cm.

*Phyllary* (*involucral bract*).—Arrangement: Imbricate. Outer bract quantity (average): 50 per inflorescence. Inner bract quantity (range): 38-75 per inflorescence. Outer bract shape: Ovate. Inner bract shape: Oblong. Margin (outer and inner bract): Entire. Outer bract texture (range): Leathery to smooth. Inner bract texture: Papyraceous. Outer bract height (average): 9 cm. Outer bract width (average): 5.75 cm. Inner bract height (average): 9 cm. Inner bract width (range): 3.25 cm. Outer bract surface (ventral and dorsal): Glabrous. Inner bract surface (ventral and dorsal): Glabrous. Outer bract color (dorsal surface): 147C and N186C. Outer bract color range (ventral surface): 157A-158A. Inner bract color range (dorsal surface): 164B to 165A. Inner bract color (ventral surface): 164D. Outer bract appearance: Matte. Inner bract appearance: Irridescent. Outer bract apex: Spinous. Outer bract base: Truncate Outer bract base width (range): 3-5 cm. Inner bract apex: Spinous. Inner bract base: Truncate. Inner bract base width (average): 2 cm. Spine color: 164B. Spine shape: Triangular. Spine dimensions: 0.25 cm. in length and 2.50 mm. in width. Receptacle diameter (average): 10 cm. Receptacle depth (average): 2 cm. Receptacle texture (after cooking): Setaceous. Receptacle color: 159B. Disc floret quantity (average): 500+. Corolla dimensions: 2.75 cm. in depth. And 0.25 cm. in diameter. Corolla color: 97A. Pappus (modified calyx): Present. Pappus appearance: Irridescent. Pappus texture: Sericeous. Pappus color: 165D. Bristle quantity (average): 500+ per capitula. Bristle shape: Filamentous. Bristle color: 165D. Bristle length (average): 5 cm. Bristle texture: Sericeous.

*Peduncle shape*.—Columnar.

*Peduncle diameter* (*average*).—3 mm.

*Peduncle color*.—147C.

*Peduncle strength*.—Rigid.

*Peduncle surface*.—Ribbed and pubescent.

Reproductive organs:

*Stamen color*.—N88D.

*Stamen length*.—2.75 cm.

*Anther diameter*.—<1 mm.

*Anther color*.—161A.

*Pollen*.—Moderate.

*Pollen color*.—164B.

*Pistil length*.—5 cm.

*Pistil color*.—N88B.

*Style color*.—N88B.

*Style length*.—2.50 cm.

*Stigma color*.—N88B.

*Stigma dimensions*.—1 mm. in height and 1 mm. in width.

*Stigma shape*.—Bifid.

*Ovary*.—Rudimentary.

*Ovary color*.—158D.

*Ovary position*.—Inferior.

Seed: None observed to date.

The invention claimed is:

1. A new and distinct cultivar of *Cynara* plant named 'PIETRO #3' as described and illustrated herein.

* * * * *